(12) United States Patent
Worthington

(10) Patent No.: US 10,098,872 B1
(45) Date of Patent: Oct. 16, 2018

US010098872B1

(54) ANALGESIC FORMULATIONS AND METHODS FOR REDUCED POSTOPERATIVE NAUSEA AND VOMITING AND ENHANCED POSTOPERATIVE PAIN RELIEF

(71) Applicant: William Bradley Worthington, Nashville, TN (US)

(72) Inventor: William Bradley Worthington, Nashville, TN (US)

( * ) Notice: Subject to any disclaimer, the term of this patent is extended or adjusted under 35 U.S.C. 154(b) by 0 days.

(21) Appl. No.: 14/997,046

(22) Filed: Jan. 15, 2016

Related U.S. Application Data

(63) Continuation-in-part of application No. 14/337,819, filed on Jul. 22, 2014, now abandoned.

(60) Provisional application No. 61/856,979, filed on Jul. 22, 2013.

(51) Int. Cl.
| | | |
|---|---|---|
| *A61K 31/445* | (2006.01) | |
| *A61K 31/135* | (2006.01) | |
| *A61K 31/407* | (2006.01) | |
| *A61M 5/14* | (2006.01) | |
| *A61M 5/142* | (2006.01) | |
| *A61M 25/00* | (2006.01) | |

(52) U.S. Cl.
CPC .......... *A61K 31/445* (2013.01); *A61K 31/135* (2013.01); *A61K 31/407* (2013.01); *A61M 5/142* (2013.01); *A61M 5/1407* (2013.01); *A61M 25/0068* (2013.01)

(58) Field of Classification Search
CPC ... A61K 31/135; A61K 31/445; A61K 31/407
USPC ........................................ 514/330, 413, 647
See application file for complete search history.

(56) References Cited

U.S. PATENT DOCUMENTS

2004/0265364 A1  12/2004  Ozturk et al.

FOREIGN PATENT DOCUMENTS

WO  2012054831 A2  4/2012

OTHER PUBLICATIONS

LeBlanc et al. Evaluation of continuous infusion of 0.5% bupivaciane by elastomeric pump for postoperative pain management after open inguinal hernia repair. J Am Coll Surg, vol. 200 No. 2 Feb. 2005 p. 198-202.*
Sveticic et al. Combinations of morphine with ketamine for patient-controlled analgesia: A new optimization method. Anesthesiology (Hagerstwon) May 2003 vol. 98. No. 5, pp. 1195-1205.
Wukovits et al. Similar analgesic effect after popliteal fossa nerve blockade with 0.375% and 0.75% bupivacaine. HSS journal: the musculoskeletal journal of Hospital for Special Surgery, (Sep. 2007) vol. 3 No. 2 pp. 173-176.
Patel et al. Comparative study of bupivacaine vs bupicacaine and ketamine (intrathecally) during intraoperative and post operative analgesia in non PIH caesarian section. National Journal of Medical Research. vol. 1 Issue 2 Oct.-Dec. 2011 ISSN 2249-4995. pp. 71-75.
Sébastien P. et al. Continuing Education in Anesthesia Critical Care and Pain 2013, 13 (1), 28-32.
Gan T. J. et al. Anesthesia & Analgesia 2014; 118:85-113.
Koivuranta M. et al. Anesthesia, 1997, 443-449.
Shaikh S. et al. Canadian Journal of Anesthesia 2003, 50(5), 514-518.
Cruthirds D. et al. Oral and Maxillofacial Surgery 2013, 115(5), 601-611.
Bion J. F. et al. Anesthesia, 1984, 39(10), 1023-1028.
Kathirvel S. et al. Anesthesia, 2000, 55(9), 899-910.
Apfelbaum, J. et al. Anesthesia Analgesia, 2003, 97:534-40.
Gan T. J, et al. Current Medical Research and Opinion 2014, 30(1), 149-160.
Nang L. et.al. Journal of Anesthesia 2014 28:790-793.
Rahmanian A. et al Neurosurgery Quarterly 2014: Nov. 6, 1-5.
PK-Beyond Cosmetic Surgery; http://drfriedberg.com/testimonials/pk-beyond-cosmetic-surgery.html; 2011.

* cited by examiner

*Primary Examiner* — Jennifer M Kim

(57) ABSTRACT

The present invention is an analgesic for pain control not limited to postoperative pain control. The present invention discloses an opioid sparing anesthetic formulation comprising a local anesthetic, an N-methyl-D-aspartate (NMDA) receptor antagonist, and a cyclooxygenase (COX) inhibitor such as Bupivacaine, Ketamine, and Ketorolac, which is effective to significantly reduce postoperative nausea and vomiting and enhance postoperative pain relief as compared to existing prior art anesthetics. The formulation is administered to a mammal in need of pain treatment. The formulation may be used as a preemptive analgesic. The analgesic formulation has a buffer for enhancing its shelf life.

8 Claims, No Drawings

ANALGESIC FORMULATIONS AND METHODS FOR REDUCED POSTOPERATIVE NAUSEA AND VOMITING AND ENHANCED POSTOPERATIVE PAIN RELIEF

CROSS REFERENCE

This application claims priority to and is a continuation-in-part of U.S. Non-Provisional application Ser. No. 14/337,819 filed Jul. 22, 2014, and claims priority to U.S. Provisional Patent Application No. 61/856,979, filed Jul. 22, 2013, the specification(s) of which is/are incorporated herein in their entirety by reference.

FIELD OF THE INVENTION

The present invention relates to an analgesic formulation for pain control not limited to postoperative pain control.

BACKGROUND OF THE INVENTION

The treatment and relief of pain is one of the most common reasons patients seek medical evaluation. Pain has been defined by the International Association for the Study of Pain as the response to real or perceived tissue trauma. The word "pain" derives from the Latin "poena," or punish. Postoperative pain is an example of acute pain. During the intraoperative period, anesthesiologists focus attention on helping abolish pain and discomfort associated with noxious stimuli and associated surgical tissue trauma. It is now recognized that many current modalities used to treat acute postoperative pain are incomplete and/or cause morbidity.

Surgical pain causes a generalized and biphasic response. The first response due to direct surgical trauma produces transduction of nociceptive input via c-fiber and a-delta activation leading to transmission, modulation and perception of pain signals in the peripheral and central nervous system. At the time of surgical trauma, complex inflammatory processes are triggered, leading to further afferent noxious input, leading to peripheral and secondary central nociceptive sensitization. This results in a reduction in the threshold of surrounding nociceptors with increased excitation and recruitment of nociceptive afferents.

Surgical trauma results in a complex local release of inflammatory mediators further contributing to peripheral sensitization and recruitment of higher threshold nociceptors, giving rise to secondary hyperalgesia; where non-painful stimuli like light touch is perceived as painful.

Central sensitization refers to processes occurring at the spinal dorsal root ganglion and higher regions of the central nervous system in response to ongoing afferent nociceptor barrage. This leads to an expansion of the nociceptive field size, increased and magnified response to nociceptive stimuli, and a reduction in the afferent stimuli threshold that is perceived as painful.

The present invention discloses an opioid sparing anesthetic formulation comprising Bupivacaine hydrochloride, Ketamine, and Ketorolac which is effective to significantly reduce postoperative nausea and vomiting and enhance postoperative pain relief as compared to existing prior art anesthetics. Without wishing to limit the present invention to any theory or mechanism, it is believed that the formulations of the present invention are advantageous because they feature drugs that, in synergism, provide long-lasting effects and are opioid-sparing.

Any feature, or combination of features, described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

In some embodiments, the present invention discloses an opioid sparing anesthetic formulation comprising Bupivacaine hydrochloride, Ketamine, and Ketorolac which is effective to significantly reduce postoperative nausea and vomiting and enhance postoperative pain relief as compared to existing prior art anesthetics. The formulations of the present invention comprise an admixture of drugs. Without wishing to limit the present invention to any theory or mechanism, it is believed that the drugs in the formulations of the present invention work together in synergism to treat pain. The combination of the drugs provides a prolonged and effective analgesia with minimal toxicity, greater ease of use, and reduced side effects. The invention is an opioid sparing innovation, As used herein, "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As defined herein, an "effective amount" means the amount of a compound that, when administered to a mammal for treating a disease, is sufficient to effect such treatment for the disease. The "effective amount" will vary depending on the compound, the disease and its severity and the age, weight, etc., of the mammal to be treated.

As defined herein, the term "agonist" refers to compound that enhances a response. The agonist binds to the same site as the endogenous compound and produces the same type of signal, usually of equal or greater magnitude than the endogenous agent. As defined herein, the term "antagonist" refers to compound that diminishes a response. The antagonist binds to the same site as the endogenous compound and diminishes or blocks the signal generated by the endogenous agent. As defined herein, the term "inhibitor" refers to an agent that slows or interferes with a chemical reaction, or a substance that reduces the activity of another substance.

As defined herein, a unit of concentration represented as "1:100,000" is equivalent to 1 mg in 1 ml or 1000 ug in 1 ml 0. For example, a concentration of 1% is equal to 10 mg/cc or 10 mg/ml, 0.5% is equal to 5 mg per cc, 0.25% is equal to 2.5 mg per cc, 0.10% is equal to 1.0 mg per cc and so forth.

As used herein, postoperative nausea and vomiting (PONV) is defined as any nausea, retching, or vomiting occurring during the first 24-48 h after surgery in inpatients[1].

It is well known in the literature that the postoperative nausea and vomiting (PONV) is the most common adverse drug effect in the immediate perioperative procedure. Gan T. J. et al.[2] and M. Koivuranta et al.[3], reported that of the patients undergoing general anesthesia, between 30% to 50% of patients suffer from PONV and this rate can increase to 80% in a high risk subset in patients undergoing general anesthesia over 24 hour period postoperatively. Therefore, there is still room for statistically significant improvement to standard of care therapies to reduce PONV.

In some embodiments, the formulation of the present invention comprises an admixture of three or more drugs. As a non-limiting example, the formulation may comprise a local anesthetic, an N-methyl-D-aspartate (NMDA) receptor antagonist, and a cyclooxygenase (COX) inhibitor.

According to some embodiments, the present invention discloses an opioid sparing anesthetic formulation comprising Bupivacaine hydrochloride, Ketamine, and Ketorolac at a concentration of 0.01% to 0.4%, 0.2 to 3 mg/ml and 0.01 to 1.0 mg/ml, respectively (hereinafter "BKK Formulation") which is much more effective in reducing PONV in compared to prior art anesthetics.

In some embodiments, the concentration of bupivacaine is about 0.125%. In some embodiments, the concentration of bupivacaine is between about 0.01% to 0.05%. In some embodiments, the concentration of bupivacaine is between about 0.025% to 0.075%. In some embodiments, the concentration of bupivacaine is between about 0.05% to 0.1%. In some embodiments, the concentration of bupivacaine is between about 0.05% to 0.125%. In some embodiments, the concentration of bupivacaine is between about 0.1% to 0.15%. In some embodiments, the concentration of bupivacaine is between about 0.1% to 0.2%. In some embodiments, the concentration of bupivacaine is between about 0.125% to 0.2%. In some embodiments, the concentration of bupivacaine is between about 0.15% to 0.25%. In some embodiments, the concentration of bupivacaine is between about 0.2% to 0.3%. In some embodiments, the concentration of bupivacaine is between about 0.3% to 0.4%. In some embodiments, the concentration of bupivacaine is more than about 0.4%.

In some embodiments, the concentration of ketamine is about 1 mg/ml. In some embodiments, the concentration of ketamine is between about 0.1 to 0.5 mg/ml. In some embodiments, the concentration of ketamine is between about 0.5 to 1.0 mg/ml. In some embodiments, the concentration of ketamine is between about 0.5 to 1.5 mg/ml. In some embodiments, the concentration of ketamine is between about 1 to 2 mg/ml. In some embodiments, the concentration of ketamine is between about 1 to 3 mg/ml. In some embodiments, the concentration of ketamine is more than 3 mg/ml and may exceed 10 mg/ml.

In some embodiments, the concentration of ketorolac is about 0.2 mg/ml. In some embodiments, the concentration of ketorolac is between about 0.01 to 1.0 mg/ml. In some embodiments, the concentration of ketorolac is between about 0.05 to 0.95 mg/ml. In some embodiments, the concentration of ketorolac is between about 0.15 to 0.95 mg/ml. In some embodiments, the concentration of ketorolac is between about 0.1 to 0.2 mg/ml. In some embodiments, the concentration of ketorolac is between about 0.2 to 0.3 mg/ml. In some embodiments, the concentration of ketorolac about 0.3 to 1.0 mg/ml. In some embodiments the concentration of ketorolac is greater than 1 mg/ml.

In some embodiments, surprisingly, more than 92% of patients treated with BKK Formulation infiltrative for Lumbar Discectomies, Decompressive Lumbar Laminectomies, Anterior Cervical Discectomies and Peripheral Nerve Decompressive Procedure surgeries reported very low to no PONV after 24 hours postoperatively. According to one embodiment, only 13.5% of the population of patients reported moderate pain, and 1.6% of the population of patients reported severe pain when they are treated with BKK formulation. Typically, 100% of patients treated with existing anesthetics for the same surgeries could still suffer noticeable PONV after 24 hours of being administered with prior art anesthetics. In fact, the significant majority of patients treated with prior art anesthetic techniques, for the same surgeries, could predictably still suffer noticeable PONV after 3 days of being administered prior art anesthetics. As used herein, the term "infiltrative analgesia" means Anesthesia produced in a local area by injecting an anesthetic agent into operative sites or wounds.

As for an example, Shaikh S, et al.[4] reported that in lumber surgery, like Lumber Micro-discectomy, the anesthesia administered intravenously were Propofol 2-2.5 mg·kg-1, Midazolam 1-2 mg, and Fentanyl 1-1.5 µg·kg-1 followed by intravenous Morphine or Ketorolac. Shaikh S. reported an incidence of postoperative nausea of 61% and postoperative vomiting of 9.4%. Most notably, 16% of patients in Shaikh's series suffered severe postoperative nausea and vomiting with a resultant hospital readmission rate of 5.7% due to severe PONV, whereas, only 0.18% patients reported severe PONV in BKK formulation with no reported hospital readmission (Table 1 below). Cruthirds D. et al.[5] also demonstrated that after outpatient surgery, the overall incidence of post discharge nausea has been reported to be 17% and of vomiting 8% which was not seen in 4000 patients treated with BKK Formulation at 24 hours postoperatively.

Recently, Patel[6] prior art demonstrated that Ketamine mixed with Bupivacaine as an injectable provided better analgesia than Bupivacaine alone. Patel publication cannot be considered as a guideline to combine Bupivacaine and Ketamine to reduce PONV because Patel further reported that in the 50 patients studied by her, 28% developed PONV in the intrathecal Bupivacaine only group, and 36% developed PONV in the intrathecal Bupivacaine plus Ketamine group. This PONV incidence of Patel as compared to the reported 4000 consecutive neurosurgical cases using Bupivacaine as the local anesthetic, Ketamine as the NMDA receptor antagonist, and Ketorolac as the non-competitive COX inhibitor used in an infiltrative block, where 92.7% of all patients at 24 hours reported no PONV (Table 1 below). Patel, et al. does not teach or suggest adding the COX inhibitor, Ketorolac in the intrathecal composition. Patel also reported from other literatures[7,6] that the administration of Ketamine, alone or in combination with other analgesics, is associated with PONV and other postoperative complications. Therefore, the Patel prior art clearly does not motivate, it is counterintuitive, to combine Ketamine with Bupivacaine in order to reduce the incidence of PONV at the time the present invention was discovered. Here, the Patel prior art simply teaches away, or in other words, Patel et al. guided researchers in an opposite direction than the direction the present invention proceeded.

Table 1 summarizes the discussion above:

TABLE 1

| PONV (nausea & vomiting for the first 24-48 hours post-surgery) | | | | |
|---|---|---|---|---|
| Formulation | % of patients with NO PONV | % of patients with SEVERE PONV | Reference | Conclusion |
| BKK | >92% | 0.18% | Present Invention | |
| Propofol, Midazolam, and Fentanyl at induction followed by | 30% | 16% | Shaikh S, et al., Can. J. Anesth. | Dramatic and superior reduction in PONV for BKK compared to |

TABLE 1-continued

PONV (nausea & vomiting for the first 24-48 hours post-surgery)

| Formulation | % of patients with NO PONV | % of patients with SEVERE PONV | Reference | Conclusion |
|---|---|---|---|---|
| intravenous Morphine or Ketorolac as additional analgesia | | | 2003 May; 50(5), 514-18 | Standard of Care |
| Bupivacaine + Saline | 72% | No data | Patel et al., National Journal of Medical Research, 2011, 1(2), 71-75. | Taught presence of Ketamine increases PONV, but BKK shows surprising result to reduce PONV |
| Bupivacaine + Ketamine | 64% | No data | | |

Clearly, one of ordinary skill would not be able to make a projection from Patel that the combination of Bupivacaine, Ketamine, and Ketorolac at a concentration of 0.01% to 0.4%; 0.2 to 3 mg/ml and 0.01 to 1.0 mg/ml respectively, would result in an anesthetic that provides statistically significant reduction in postoperative PONV where 92.7% of all patients reported no PONV, 0% reported mild, 5.37% reported moderate and 0.18% reported severe PONV.

In some embodiments, the local anesthetic comprises bupivacaine hydrochloride. In some embodiments, the local anesthetic comprises lidocaine, ropivacaine, prilocaine, amethocaine, procaine, cinchocaine, mepivacaine, etidocaine, or any other long acting local anesthetic. In some embodiments, the NMDA receptor antagonist comprises ketamine, trilamine, tramadol, or any other phencyclidine derivative. In some embodiments, the COX inhibitor comprises ketorolac, acetaminophen, paracoxib, ibuprofen or any other drug in this class.

It is will documented in the literature that postoperative pain can have a significant impact on patient recovery. Apfelbaum, J. et al.[9] reported of the approximately 73,000,000 surgeries performed in the United States each year, 80% of those patients experience postoperative pain from the immediate postoperative period until 2 weeks after discharge. Of those patients studied by Apfelbaum, 86% reported moderate, severe, or extreme pain and 25% of those patients who received standard of care opioid-based analgesia reported an adverse drug related effect. Gan T. J, et al[10] interviewed 300 patients having surgery within the previous five years finding 86% experienced pain after surgery and of these, 75% reported moderate to extreme pain immediately post-operation, with 74% experiencing pain after discharge. Therefore, there is an urgent need to develop an improved analgesic formulation to significantly reduce postoperative pain for patients undergoing surgeries.

In some embodiments, the present invention discloses an opioid sparing anesthetic formulation comprising Bupivacaine hydrochloride, Ketamine, and Ketorolac (hereinafter "BKK Formulation") at a concentration of 0.01% to 0.4%, 0.2 to 3 mg/ml and 0.01 to 1.0 mg/ml, respectively which is effective to reduce postoperative Pain significantly as compared to existing prior art ananesthetic compositions.

In some embodiments, the concentration of bupivacaine is about 0.125%. In some embodiments, the concentration of bupivacaine is between about 0.01% to 0.05%. In some embodiments, the concentration of bupivacaine is between about 0.025% to 0.075%. In some embodiments, the concentration of bupivacaine is between about 0.05% to 0.1%. In some embodiments, the concentration of bupivacaine is between about 0.05% to 0.125%. In some embodiments, the concentration of bupivacaine is between about 0.1% to 0.15%. In some embodiments, the concentration of bupivacaine is between about 0.1% to 0.2%. In some embodiments, the concentration of bupivacaine is between about 0.125% to 0.2%. In some embodiments, the concentration of bupivacaine is between about 0.15% to 0.25%. In some embodiments, the concentration of bupivacaine is between about 0.2% to 0.3%. In some embodiments, the concentration of bupivacaine is between about 0.3% to 0.4%. In some embodiments, the concentration of bupivacaine is more than about 0.4%.

In some embodiments, the concentration of ketamine is about 1 mg/ml. In some embodiments, the concentration of ketamine is between about 0.1 to 0.5 mg/ml. In some embodiments, the concentration of ketamine is between about 0.5 to 1.0 mg/ml. In some embodiments, the concentration of ketamine is between about 0.5 to 1.5 mg/ml. In some embodiments, the concentration of ketamine is between about 1 to 2 mg/ml. In some embodiments, the concentration of ketamine is between about 1 to 3 mg/ml. In some embodiments, the concentration of ketamine is more than 3 mg/ml and may exceed 10 mg/ml.

In some embodiments, the concentration of ketorolac is about 0.2 mg/ml. In some embodiments, the concentration of ketorolac is between about 0.01 to 1.0 mg/ml. In some embodiments, the concentration of ketorolac is between about 0.05 to 0.95 mg/ml. In some embodiments, the concentration of ketorolac is between about 0.15 to 0.95 mg/ml. In some embodiments, the concentration of ketorolac is between about 0.1 to 0.2 mg/ml. In some embodiments, the concentration of ketorolac is between about 0.2 to 0.3 mg/ml. In some embodiments, the concentration of ketorolac about 0.3 to 1.0 mg/ml. In some embodiments the concentration of ketorolac is greater than 1 mg/ml.

According to some embodiments, surprisingly, more than 25% of patients treated with BKK Formulation infiltrative for Lumbar Disectomies, Decompressive Lumbar Laminectomies, Anterior Cervical Discectomies with fusion and Peripheral Nerve Decompressive Procedures surgeries reported NO PAIN after 24 hours in 4000 consecutive neurosurgical cases. Among these same 4000 consecutive neurosurgical cases, at 24 hours postoperatively, 59.4% patients reported mild pain, 13.5% patients reported moderate pain, and only 1.6% reported severe pain. The discovery that opioid sparing BKK is an effective anesthetic that abolishes pain completely in more than 25% cases and allows severe pain in only 1.6% cases after 24 hours post-surgery is surprising because there is nothing in the medical and scientific literature that suggests the combination of the three ingredients would render this statistically significant and surprising result.

Recently, Wang prior art[11] disclosed that sixty-two patients undergoing total hip arthroplasty with spinal anesthesia were given either 13.5 mg hyperbaric Bupivacaine with normal Saline or 13.5 mg hyperbaric Bupivacaine with 2 mg preservative-free Ketorolac. The results suggest that the pain during the first 2 days after surgery did not differ between the Ketorolac and Saline groups, importantly the postoperative opioid use did not differ between the Ketorolac and Saline groups also (Table 2 below). Wang reported the presence and area of hyperalgesia and allodynia surrounding the wound obtained at 48 h postoperatively. Therefore, the inefficiency of Ketorolac to reduce postoperative pain, when it is combined with Bupivacaine as compared to Bupivacaine alone, clearly shows that a motivation is lacking, it would be counterintuitive, to combine Ketorolac and Bupivacaine at the time the present invention was discovered. Wang prior art is also pointing researchers in an opposite direction than the direction the inventor proceeded. In other words, Wang et. al. teaches away from the proposed combination of Bupivacaine, Ketamine and Ketorolac as a multimodal analgesic composition as claimed in the present invention to reduce postoperative pain significantly.

In another literature, Rahmanian et al.[12] disclosed the ineffectiveness of Local Infiltrative Bupivacaine in Lumbar Laminectomy. Rahmanian reported that 30 mL of 0.25% Bupivacaine hydrochloride administered as an infiltrative field block at the time of surgical closure was no more effective than 30 ml normal Saline in decreasing postoperative surgical pain. Pain was assessed at rest using subjective linear VAS scores. In Rahmanian prior art, VAS scores in the Bupivacaine group were more than the control Saline group (Table 2 below). The Rahmanian reported findings, compared to those reported using BKK in the exact same surgical procedure, are disruptive, clinically counterintuitive and contrary.

Table 2 summarizes the discussion above:

Clearly, one of ordinary skill would not be able to make a projection from Wang and/or Rahmanian that the combination of bupivacaine hydrochloride, ketamine, and ketorolac at a concentration of 0.01% to 0.4%; 0.2 to 3 mg/ml and 0.01 to 1.0 mg/ml respectively, would result in an anesthetic that causes no pain in more than 25% of patients 24 hours post-surgery, mild pain in 59.4%, moderate pain in 13.5% and severe pain in only 1.6% treated patients 24 hours postoperatively. The Wang/Rahmanian reported findings compared to those reported using BKK in the exact same surgical procedure are disruptive, clinically counterintuitive, contrary, whereas BKK formulation clearly provides a statistically significant improvement to standard of care therapies.

In some embodiments, the BKK formulation further comprises a saline solution. In some embodiments, bupivacaine is added to the saline solution at a desired concentration. In some embodiments, ketorolac and ketamine is added to the bupivacaine and saline solution.

As a non-limiting example, an analgesic formulation may comprise 0.25% bupivacaine with 1:400,000 epinephrine, 0.2 mg/ml ketorolac, and 1 mg/ml of ketamine.

The following is a non-limiting example of preparing the analgesic formulation in a 60 cc syringe containing 0.25% bupivacaine with 1:400,000 epinephrine, 0.2 mg/ml ketoralac, and 1 mg/ml of ketamine:

1. Dilute 30 ml of 0.5% bupivacaine, epinephrine 1:200,000 into 29 cc preservative free normal saline (NS);
2. Add 0.4 ml of ketorolac 30 mg/cc;
3. Add 0.6 ml of ketamine 100 mg/cc.

In some embodiments, the formulation further comprises a transient potential vanilloid (TRPV) receptor agonist or antagonist. In some embodiments, the TRVP agonist is capsaicin or resiniferatoxin or any other agonist. In some embodiments, the TRVP antagonist is capazepine or any other arylurea cinnamide, or caroxamide antagonist. In some embodiments, the formulation further comprises a protein kinase inhibitor. In some embodiments, the protein kinase inhibitor is timsirolimus. In some embodiments, the formu-

TABLE 2

| PAIN RELIEF POST OPERATIVELY AFTER PAINFUL PROCEDURES | | | | | |
|---|---|---|---|---|---|
| Formulation | Patients with NO PAIN | Patients with MILD PAIN/ | Time | Reference | Conclusion |
| BKK | 25.4% | 59.4% | 24 hr | Present Invention | |
| Bupivacaine + Ketorolac intrathecal and intravenous moiphine or hydromorphone with subsequent oral oxycodone 24 hr. Postoperative. | 0% | 0% | 24 hr | Wang, et. al. J. Anesth. 2014 28: 790-793 | Bupivacaine + Ketorolac combination intrathecal is not more effective than bupivacaine + saline intrathecal combination in reducing post-operative pain. But the combination of BKK shows surprising result to reduce postoperative pain. |
| Bupivacaine Infiltrative Block | 0% | 0% | 12 hr | Rahmanian, et al. Neuro. Surg. Quarterly; 2014: Nov. 6 | 30 mL of 0.25% Bupivacaine Hydrochloride was no more effective than 30 ml Normal Saline in decreasing postoperative surgical pain. But the combination of BKK shows surprising result to reduce postoperative pain. |
| Saline Infiltrative Block | 0% | 0% | | | | lation further comprises a competitive or non-competitive glycine or glutamate antagonist. Non-limiting examples of the competitive or non-competitive glycine or glutamate antagonist are magnesium, ramacemide, and tiletamine. In some embodiments, the formulation further comprises acetaminophen or paracetamol.

In some embodiments, the BKK formulation has an increased shelf life as compared to the shelf lives of the individual components of the formulation. In some embodiments, the BKK formulation comprises a buffer for enhancing shelf life. In some embodiments, the formulation comprises a buffer for raising or lowering the pKa of the formulation. Buffers are used to control a pH of a formulation by preventing pronounced variations in pH during use or storage. Preferably, the buffers may buffer the formulation from a pH of about 7.3 to a pH of about 7.6, more preferably from a pH of about 7.35 to a pH of about 7.5, and most preferably from a pH of about 7.3 to a pH of about 7.4. Non-limiting examples of buffers include citric acid, triethanolamine, acetates, and phosphates.

In some embodiments, the BKK formulation further comprises epinephrine. In some embodiments, a concentration of epinephrine is between about 1:200,000 to 1:800,000. In some embodiments, the BKK formulation further contains and comprises a beta-lactam antibiotic.

Without wishing to limit the present invention to any theory or mechanism, it is believed that the BKK formulation of the present invention has a bactericidal and/or a bacteriostatic effect.

In some embodiments, the BKK formulation of the present invention is used as a preemptive analgesic. Preemptive analgesics are administered prior to the onset of nociceptive stimulus as a means to prevent or reduce subsequent pain.

In some embodiments, the BKK formulation is directly injected, e.g., at the surgical incision and/or surrounding tissues. In some embodiments, the BKK formulation is injected via the subcutaneous route, the intramuscular (IM) route, the intradermal route, or any other appropriate route. In some embodiments, the BKK formulation is delivered via a catheter and/or a pump (e.g., elastomeric pump or digital electronic pump). In some embodiments, the BKK formulation is administered to a site prior to a needle insertion, an incision, or other medical procedures.

In some embodiments, the BKK formulation is administered at or adjacent to the sites of pain to provide relief. In some embodiments, the BKK formulation is administered once a day, for example, for fast, temporary pain relief or more frequently, such as twice or three times a day, to maintain pain relief over an extended period of time. In some embodiments, the BKK formulation is administered between about every 3 to 6 hours until the pain completely subsides. In some embodiments, for clinical purposes, the volume of the BKK formulation used as a single infiltration may vary from between about 0.1 mL to 1000 mL. In some embodiments, the volume of the BKK formulation used as a single infiltration may vary from between about 10 to 1000 mL. In some embodiments, the volume of the BKK formulation used as a single infiltration may vary from between about 100 to 1000 mL. In some embodiments, the volume of the BKK formulation used as a single infiltration may vary from between about 500 to 1000 mL. In some embodiments, the volume of the BKK formulation used as a single infiltration may vary from between about 0.1 to 100 mL. In some embodiments, the volume of the BKK formulation used as a single infiltration may vary from between about 0.1 to 10 mL.

The volume of BKK formulation may depend on a patient's weight and the required effective minimal concentration of the formulation. In one embodiment, the required effective minimal concentration of the BKK formulation components is 0.048 to 0.149% of the local anesthetic bupivacaine, 0.12 mg/kg of the N-methyl-D-aspartate (NMDA) receptor antagonist, and 0.4 mg/kg of the cyclooxygenase (COX) inhibitor. As a non-limiting example, a patient weighing 160 pounds and having a lumbar spinal procedure may be administered 60 mL at a concentration of bupivacaine 0.25%, ketorolac 0.02%, and ketamine 0.1%.

In some embodiments, the BKK formulation may be delivered as a continuous infusion for delivering the formulation to targeted soft tissue including skin, subcutaneous tissue and fat, fascial planes, bone, and peripheral sensory nerves. In some embodiments, continuous infusion rates of the formulation vary from 1.0 mL to 100 mL per hour. In some embodiments, continuous infusion rates of the formulation vary from 1.0 mL to 10 mL per hour. In some embodiments, continuous infusion rates of the formulation vary from 10 mL to 50 mL per hour. In some embodiments, continuous infusion rates of the formulation vary from 50 mL to 100 mL per hour. In some embodiments, the formulation is administered intradermally, using, for example, a syringe.

In some embodiments, the BKK formulation is used at any location in the body where pain reduction is required or desirable. In some embodiments, the BKK formulation is used to treat pain, other than neuropathic pain. This would apply to pain cause by injuries, such as wounds and burns, and areas where medical procedures, dental procedures and cosmetic procedures are performed. For example, the BKK formulation may be administered to a patient having an abrasion, cut, puncture wound, or other skin or soft tissue wound that causes pain. As another example, burns also cause pain and administering the BKK formulation would rapidly reduce the pain.

The following is a non-limiting example of administering said formulation to a patient requiring surgery, for example, decompressive lumbar laminectomy with fusion:

Preoperative Period

1. The patient is injected at or near the surgical site with 30 to 60 cc's of the BKK formulation 2 hours prior to the surgical procedure.

Interoperative Period

2. The patient is injected with 60-80 cc of the BKK formulation as an infiltrative field block at the time of wound closure.

Postoperative Period

3. The patient is administered a continuous infusion of the BKK formulation delivered through a catheter system incorporated into the tissue involved with the surgical incision.

In some embodiments, the BKK formulation is utilized in veterinary applications. In some embodiments, the formulation is administered to animals such as dogs, cats, horses, rabbits, or other mammals. In some embodiment, the BKK formulation is utilized in dental applications. For example, in order to relieve the pain from an extraction, the BKK formulation may be injected to a patient's gums prior to extracting a tooth.

As used herein, the term "about" refers to plus or minus 10% of the referenced number.

Various modifications of the invention, in addition to those described herein, will be apparent to those skilled in the art from the foregoing description. For example, reference to USPTO US2009/0093669 A1 may be applied to enable the invention to be actively delivered transdermally. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

1. Sébastien P. et al. Continuing Education In Anesthesia Critical Care and Pain 2013, 13 (1), 28-32.
2. Gan T. J. et al. Anesthesia Analgesia 2014; 118:85-113.
3. Koivuranta M. et al. Anesthesia, 1997, 443-449.
4. Shaikh S. et al. Canadian Journal of Anesthesia 2003, 50(5), 514-518.
5. Cruthirds D. et al. Oral Surgery Oral Medicine Oral Pathology Oral Radiology 2013, 115(5). 601-611.
6. Patel I. et al. National Journal of Medical Research, 2011, 1(2), 71-75.
7. Bjon J. F. et al. Anesthesia, 1984, 39(10), 1023-1028.
8. Kathirvel S. et al. Anesthesia, 2000, 55(9), 899-904.
9. Apfelbaum, J. et al. Anesthesia Analgesia, 2003, 97:534-40.
10. Gan T. J, et al. Current. Medical. Research and Opinion. 2014, 30(1), 149-160.
11. Wang L. et al. Journal of Anesthesia 2014 28:790-793.
12. Rahmanian A. et al Neurosurgery Quarterly 2014: Nov. 6, 1-5.

What is claimed:

1. A method for reducing post-operative nausea and vomiting in human patients and providing a multimodal infiltrative opioid sparing analgesic infiltration, the method consisting essentially of the steps of:
   a) administering an effective amount of a multimodal infiltrative formulation into and around a surgical site, the multimodal infiltrative formulation consisting essentially of:
      (i) a local anesthetic being a bupivacaine, wherein the concentration of bupivacaine is between 0.2% to 0.3%;
      (ii) an N-methyl-D-aspartate (NMDA) receptor antagonist being a ketamine, wherein the concentration of ketamine is between about 1.0 to 3.0 mg/ml; and
      (iii) a cyclooxygenase (COX) inhibitor being a ketorolac, wherein the concentration of ketorolac is about 0.3 to 1.0 mg/ml
   b) injecting the multimodal infiltrative formulation as an infiltrative field block at the time of a wound closure, wherein the infiltrative analgesic procedure eliminates/reduces the use of opioids to treat post-operative pain, wherein more than 90% of human patients who underwent the infiltrative analgesic procedure experienced no nausea and vomiting at 24 hours post-operatively, and over 85.8% report no or mild pain at 24 hours after surgery.

2. The method of claim 1, wherein the local anesthetic consists essentially of bupivacaine hydrochloride, wherein the NMDA receptor antagonist comprises ketamine, and wherein the COX inhibitor comprises ketorolac.

3. The method of claim 2, wherein the concentration of bupivacaine hydrochloride is between about 0.2% to 0.3%.

4. The method of claim 2, wherein the concentration of ketamine is between about 1.0 to 3.0 mg/ml.

5. The method of claim 2, wherein the concentration of ketorolac is about 0.3 to 1.0 mg/ml.

6. The method of claim 1, wherein the multimodal formulation is infiltrated into and around soft tissue, fascia, subcutaneous fat, muscle, or dermal tissue planes.

7. The method of claim 1, wherein the population of human patients reported no post-operative nausea and vomiting at 24 hours is 92.6%, wherein the population of human patients reported no post-operative nausea and vomiting at 24 hours is 92.5%, wherein the population of human patients reported no post-operative nausea and vomiting at 24 hours is 92.4%.

8. The method of claim 1 further consisting essentially of a step of inserting a multi-orifice dual catheter at the surgical site to continuously infuse the multimodal infiltrative formulation through an elastomeric/digital pump at the completion of a surgery.

* * * * *